(12) United States Patent
Norton et al.

(10) Patent No.: US 7,248,920 B2
(45) Date of Patent: Jul. 24, 2007

(54) APPARATUS AND METHOD FOR EXERCISING A BATTERY FOR AN IMPLANTABLE MEDICAL DEVICE

(75) Inventors: John D. Norton, New Brighton, MN (US); Craig L. Schmidt, Eagan, MN (US)

(73) Assignee: Medtronic, Inc., Minneapolis, MN (US)

(*) Notice: Subject to any disclaimer, the term of this patent is extended or adjusted under 35 U.S.C. 154(b) by 439 days.

(21) Appl. No.: 10/773,391

(22) Filed: Feb. 6, 2004

(65) Prior Publication Data

US 2005/0177198 A1 Aug. 11, 2005

(51) Int. Cl.
*A61N 1/39* (2006.01)
(52) U.S. Cl. ............................. 607/5; 429/49
(58) Field of Classification Search ................ 607/4–5, 607/7, 9, 29, 34
See application file for complete search history.

(56) References Cited

U.S. PATENT DOCUMENTS

| | | | |
|---|---|---|---|
| 3,082,360 A | 3/1963 | Robinson et al. | |
| 3,688,161 A | 8/1972 | Gerhart et al. | |
| 4,568,869 A * | 2/1986 | Graham, Jr. ................ | 320/139 |
| 5,904,705 A * | 5/1999 | Kroll et al. ..................... | 607/5 |
| 6,112,117 A * | 8/2000 | KenKnight et al. ............. | 607/5 |
| 6,130,005 A | 10/2000 | Crespi et al. | |
| 6,283,985 B1 | 9/2001 | Harguth et al. | |
| 6,409,796 B1 | 6/2002 | Surpin et al. | |
| 6,807,048 B1 | 10/2004 | Nielsen et al. | |
| 2004/0161671 A1* | 8/2004 | Merritt et al. ............. | 429/326 |
| 2006/0051659 A1* | 3/2006 | Kelly et al. .................. | 429/56 |

FOREIGN PATENT DOCUMENTS

| | | |
|---|---|---|
| EP | 0447165 | 9/1991 |
| EP | 0503778 | 9/1992 |
| GB | 1100614 | 1/1968 |
| JP | 03203523 | 8/2006 |

* cited by examiner

*Primary Examiner*—Carl Layno
(74) *Attorney, Agent, or Firm*—Paul H. McDowall; Girma Wolde-Michael

(57) ABSTRACT

A method and apparatus exercise a battery of an implantable medical device by determining whether a film is disposed on a portion of an electrode of a battery, discharging the battery a sufficient amount to reduce the film, and optimizing energy used during exercising the battery. The apparatus includes a battery having an electrode that develops a resistive film and a low deformation rate capacitor capable of storing a charge from the battery, the capacitor requiring few or no periodic discharges of the battery for reformation. The energy from the battery is periodically discharged into the low deformation-rate capacitor to reduce film buildup on the electrode.

34 Claims, 9 Drawing Sheets

APPARATUS AND METHOD FOR EXERCISING A BATTERY FOR AN IMPLANTABLE MEDICAL DEVICE

FIELD OF THE INVENTION

The present invention relates to the field of medical devices. More particularly, the present invention relates to a system for selectively exercising the battery of a battery-powered medical device, such as an implantable cardiac defibrillator (ICD), based on the charge delivery performance of the battery so as to maintain charge delivery performance while conserving battery energy.

BACKGROUND OF THE INVENTION

Medical devices are used to treat patients suffering from a variety of conditions. Examples include implantable medical devices (IMDs) such as implantable pacemakers and ICDs, which are electronic medical devices monitoring the electrical activity of the heart and, when necessary, providing therapeutic electrical stimulation to one or more of the heart chambers. For example, a pacemaker senses an arrhythmia episode (i.e., a disturbance in heart rhythm) and provides appropriate therapeutic electrical stimulation pulses, at a controlled rate, to selected chambers of the heart in order to terminate the arrhythmia and restore the proper heart rhythm. The types of arrhythmias detected and corrected by pacemakers include bradycardia, which are unusually slow heart rates, and tachycardia, which are unusually fast heart rates.

Medical devices such as ICDs also detect arrhythmias and provide appropriate electrical stimulation pulses to selected chambers of the heart to correct the abnormal heart rate and/or rhythm. In contrast to pacemakers, however, an ICD can also deliver much stronger and less frequent pulses of therapeutic electrical stimulation (e.g., cardioversion and/or defibrillation therapy). This is because ICDs are generally designed to terminate episodes of cardiac fibrillation (e.g., episodes of rapid, unsynchronized quivering of one or more heart chambers) and severe tachycardia (e.g., very rapid but relatively coordinated contractions of the heart). To correct such arrhythmias, an ICD delivers a low, moderate, and/or high-energy electrical therapy to the heart.

The typical defibrillator or cardioverter includes a set of electrical leads, which extend from a sealed housing into operative contact with a portion of a heart. Within the housing are a battery for supplying power, one or more capacitors coupled to the battery and adapted to rapidly deliver bursts of electric energy via the leads to the heart, and monitoring circuitry for monitoring cardiac activity and determining when, where, and what electrical therapy to withhold or apply. The monitoring circuitry generally includes a microprocessor and a computer readable memory medium storing instructions not only dictating how the microprocessor answers therapy questions, but also controlling certain device maintenance functions, such as maintenance of the capacitors in the device.

With respect to ICDs, typically at least two capacitors are electrically coupled to the heart. One type of capacitor adapted for use in conjunction with an ICD includes aluminum electrolytic capacitors, although other types have been used as well. This type of capacitor usually includes sheets of aluminum foil and electrolyte-impregnated separator material. Each strip of aluminum foil is covered with an aluminum oxide, which insulates the foils from the electrolyte in the paper. One maintenance issue with aluminum electrolytic capacitors concerns the degradation of their charging efficiency after long periods of inactivity. The degraded charging efficiency, which stems from instability of the aluminum oxide in the liquid electrolyte, ultimately requires the battery to progressively expend more and more energy to charge the capacitors prior to delivering cardioversion or defibrillation therapy.

Thus, to repair this oxide degradation, microprocessors are typically programmed to reform the degraded (or deformed) aluminum oxide. The capacitor reform process typically involves at least one capacitor charge-discharge cycle. For example, an aluminum capacitor is typically rapidly charged and held at or near a rated or maximum-energy voltage (the voltage corresponding to maximum energy) for a time period (e.g., on the order of less than about one minute), before being discharged internally through a non-therapeutic load. In some cases, the maximum-energy voltage is allowed to leak off slowly rather than being maintained; in others, it is allowed to leak off (or droop) for 60 seconds and discharged through a non-therapeutic load; and in still other cases, the voltage is alternately held for five seconds and drooped for 10 seconds over a total period of 30 seconds, before being discharged through a non-therapeutic load. These periodic charge-hold-discharge (or charge-hold-droop-discharge) cycles for capacitor maintenance are referred to as "reforming." Unfortunately, reforming aluminum electrolytic capacitors tends to reduce battery life.

The aluminum electrolytic capacitors used in early ICDs exhibited relatively low energy density (<2 J/cc) and therefore contributed a large amount to the overall device volume. To decrease capacitor and ICD volume, medical device designers, suppliers and manufacturers developed implantable wet-tantalum capacitors. In addition to having a higher energy density (>4 J/cc) such capacitors exhibit a slightly lower rate of de-formation, and therefore require less energy to effectively reform the oxide layer of the capacitor. More recently, wet-tantalum capacitors that require very little or no reformation have been developed. To wit, non-provisional U.S. patent application Ser. No. 10/448,594 filed 30 May 2003 and entitled, "WET TANTALUM CAPACITOR USABLE WITHOUT REFORMATION AND MEDICAL DEVICES FOR USE THEREWITH" and non-provisional U.S. patent application Ser. No. 10/431,356 filed 7 May 2003 entitled, "WET TANTALUM REFORMATION METHOD AND APPARATUS" are directed to such subject matters, and the contents of each are hereby entirely incorporated by reference herein.

While substantially eliminating the need for capacitor reformation, these low or non-reformation capacitors may contribute to energy-management issues within an ICD. For example, capacitors not requiring reformation can cause the ICD battery to operate without a high current pulse for a long period of time (e.g., months to years). Most implantable device batteries are comprised of Li/SVO (lithium/silver vanadium oxide), a lithium anode, and a silver vanadium oxide cathode. When there is an extended period between high voltage therapies or other high current events, the battery can develop a deleterious resistive film on the surfaces of an anode disposed within the battery. First, the lithium anode forms its own passive film by reaction with electrolyte. This film, commonly referred to as the solid electrolyte interface (SEI), is typically harmless since it comprises an electrically conductive film. However, the SEI film can increase in thickness over time, and thus contribute increased electrical resistance to the operative circuitry of an ICD.

Second, the SVO material also forms a film on the lithium surface. This is equally undesirable as it results in further increases in film thickness and in electrical resistance over time. Generally, these problems are resolved during the reformation process or as a result of one or more high current pulses, during which the resistive film will dissipate (or "slough off") thus providing a fresh lithium surface.

However, if an IMD uses a capacitor that does not require reformation, then over time the above-mentioned SEI films can be expected to only increase in size and electrical resistance. If this occurs, subsequent high-current pulses will suffer from "voltage delay" due to the increased resistance of the films. Voltage delay occurs when the highly resistive SEI film causes the voltage delivered during a high current pulse to be lower than a desired magnitude (e.g., less energy than that which would be delivered in the absence of resistive SEI film). This voltage delay will occur until the film sloughs off the lithium. Voltage delay is undesirable in that it causes the battery to take longer to charge the capacitor and reduces battery life. For example, if the battery voltage is lower during the high current pulse, it is delivering less energy per unit time. Therefore, it takes more charge out of the battery to provide the pulse and it takes longer to charge the capacitor. This problem is exacerbated the longer the battery goes without a capacitor reformation or a high current pulse.

Another problem is created if the battery voltage is too low. In most ICDs there is a minimum voltage or a voltage floor representing the voltage necessary to continue to power the ICD circuitry while the capacitor is being charged. Generally, if the battery voltage drops below this voltage floor, a power-on-reset (POR) can occur where the ICD will suspend any therapy currently in progress. To combat this problem ICDs will generally implement a safety feature, which prevents the battery voltage from dropping below the voltage floor by lowering the current drawn from the battery when the battery voltage approaches the voltage floor. However, by drawing less current from the battery the process of charging the capacitor is lengthened. This is undesirable as it is commonly accepted that the odds of survival or recovery from a potentially lethal arrthymia such as ventricular fibrillation (VF) decrease significantly as the amount of time taken to deliver a cardiac therapy to terminate an episode of VF increases. A voltage delay may exacerbate this problem in two ways. First, the voltage delay would increase the time required to charge the capacitor by reducing available battery power. Second, a voltage delay may cause the battery voltage to drop below the voltage floor thus initiating the POR safety feature, further reducing available battery power and increasing capacitor charge time. This could potentially prevent an appropriate therapy from even being administered as some devices will either cease charging, or deliver a reduced energy after a predetermined charge interval.

Yet another potential adverse impact of voltage delay is reduced device longevity. Typically ICDs are designed to declare the Elective Replacement Indicator (ERI) when the background voltage of the battery (voltage in the absence of capacitor charging) reaches a predetermined level. However, most devices incorporate a secondary mechanism for declaring ERI when the capacitor charge time reaches a predetermined, excessively high level. In the event that voltage delay results in such an excessively long charge time, these devices will trigger the ERI well before battery depletion, significantly reducing the longevity of the ICD. Therefore, a voltage delay not only delays the delivery of a cardiac therapy it also has an impact on the overall device operation.

In prior ICDs the energy required to reform the capacitor was much greater than that required to remove the anode film from the battery, and therefore dominated any increase in capacitor charge time. Furthermore, the need to frequently reform the capacitor provided the required periodic conditioning of the battery necessary to minimize the effects of voltage-delay. However, now that capacitors needing little to no reformation have been developed, the potential exists for voltage-delay to become substantial, resulting in extended capacitor charge times when long periods of time pass between capacitor charging or other high current drain events driven by the battery. Changing trends within the industry may further exacerbate this. As ICDs have evolved, detection algorithms and therapies have become more sophisticated. As a result, devices are more frequently treating potentially fatal arrhythmias with alternative low-energy therapies (e.g., so-called anti-tachycardia pacing or "ATP"), thereby dramatically reducing the number of high-energy therapies being administered. In addition, indications for ICD implantation have been expanded to include patients who are expected to require only very few high-energy cardioversion or defibrillation therapies over the life of the device.

BRIEF SUMMARY OF THE INVENTION

An implantable medical device in embodiments according to certain embodiments of the invention may include one or more of the following features: (a) a battery having an electrode that develops a resistive film (b) a low deformation-rate capacitor capable of storing a charge from the battery, the capacitor requiring few periodic discharges of the battery for reformation, (c) a means for periodically discharging the battery to reduce film buildup on the electrode, (d) a lead for sensing electrical signals of a patient through the lead, (e) a status system for monitoring heart activity of the patient through the lead, (f) a therapy delivery system for delivering electrical energy through the lead to a heart of the patient, (g) a means for determining elapsed time since a therapy was delivered to a patient or when the battery was discharged to remove electrode film buildup, (h) a means for optimizing the battery discharge, and (i) a means for optimizing the time between discharging the battery.

An implantable cardioverter defibrillator according to one or more embodiments of the present invention may include one or more of the following features: (a) a lead for applying electrical energy to the patient, (b) a battery having an electrode for powering the implantable cardioverter defibrillator, the battery having an electrode that develops a film on it over time due to a lack of battery discharge, (c) an ICD status system for monitoring heart activity of the patient through the lead, (d) a therapy delivery system for delivering electrical energy through the lead to a heart of the patient, (e) a capacitor capable of storing a charge from the battery, the capacitor requiring no periodic discharges of the battery for reformation, (f) means for periodically discharging the battery to prevent film buildup on the electrode, (g) a means for determining elapsed time since a therapy was delivered to a patient or when the battery was discharged to remove electrode film buildup, (h) a means for optimizing the battery discharge, and (i) a means for optimizing the time between discharging the battery.

A computer readable storage medium according to certain embodiments of the present invention can include executable instructions for performing one or more of the following: (a) instructions for applying therapeutic electrical energy to a patient via one or more electrical medical leads, (b) instructions for powering an ICD with a primary battery cell, wherein the battery cell develops an electrically resistive film over time due to a lack of relatively high current drain (e.g., battery discharge), (c) instructions for monitoring heart activity of the patient through the medical electrical lead, (d) instructions for operating a therapy delivery system adapted to deliver electrical energy through a lead adapted to be coupled a patient's myocardium, (e) instructions for storing electrical charge in a capacitor delivered from the battery cell, wherein the capacitor requires essentially no periodic discharges for capacitor reformation, (f) means for periodically discharging the battery to prevent film buildup on the electrode, (g) a means for determining elapsed time since a therapy was delivered to a patient or when the battery was discharged to remove electrode film buildup, (h) a means for optimizing the battery discharge, and (i) a means for optimizing the time between discharging the battery.

A method of exercising a battery for an implantable medical device according to the present invention may include one or more of the following steps: (a) determining whether a film may have built up on an electrode of the battery, (b) discharging the battery to reduce film build up on the electrode of the battery, (c) optimizing energy used during exercising the battery, and (d) optimizing the time period between exercising to extend the life of the battery.

DETAILED DESCRIPTION OF THE ILLUSTRATED EMBODIMENTS

Figure 1:
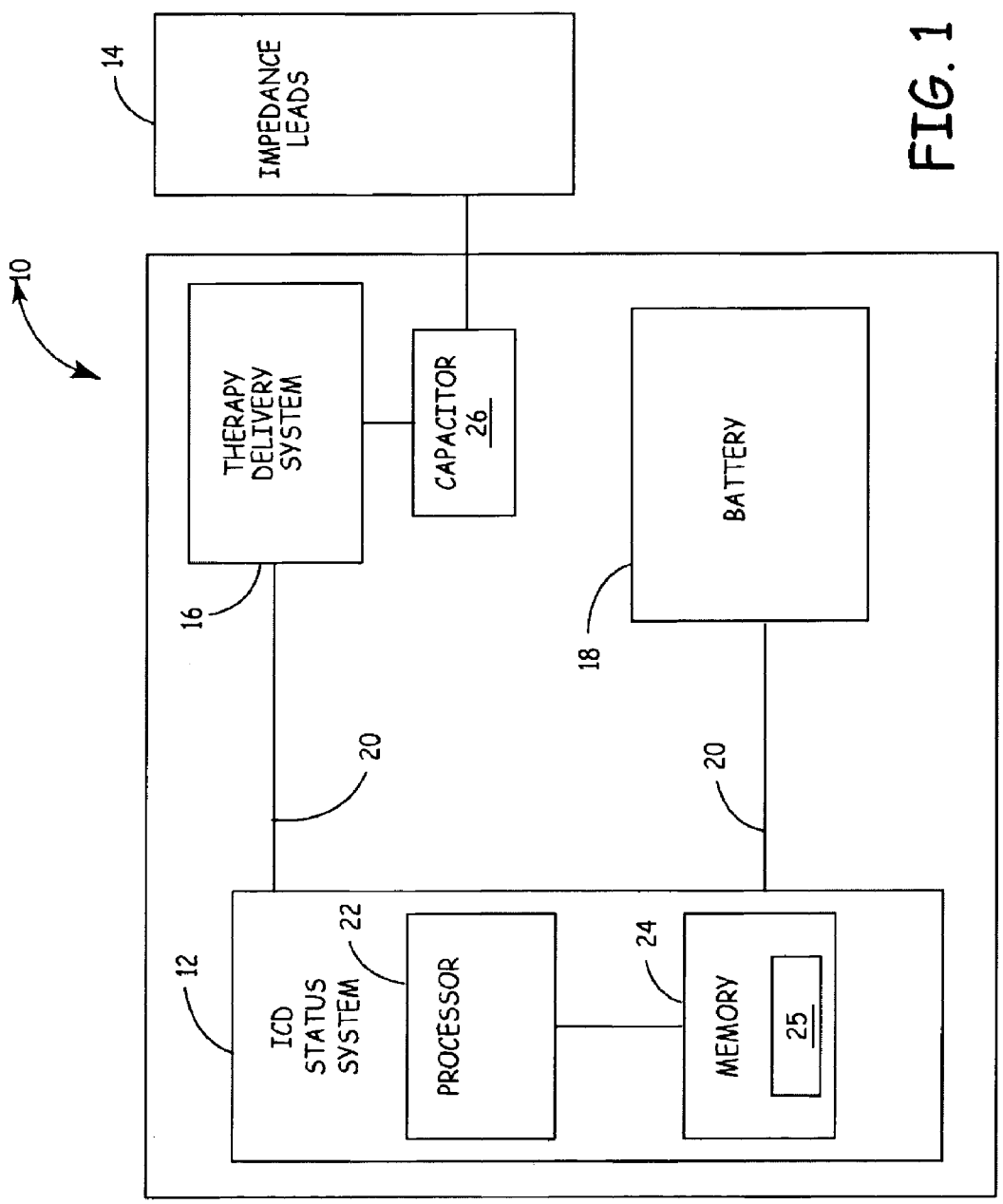
FIG. 1 is a simple block diagram illustrating an implantable cardioverter defibrillator according to an embodiment of the present invention.

The following discussion of the illustrated embodiments is intended to enable a person skilled in the art to make and use the claimed invention. Various modifications to the illustrated embodiments will be readily apparent to those skilled in the art, and the generic principles herein may be applied to other embodiments and applications without departing from the spirit and scope of the present invention as defined by the appended claims. For example, those skilled in the art will appreciate that various materials, components and system architectures may be used to practice the invention. Accordingly, the present invention is not intended to be limited to just the illustrated embodiments, but should be accorded the widest scope consistent with the principles and features disclosed herein as well as those inherent in the subject matter described, as understood by those of skill in the art. The following detailed description is to be read with reference to the figures, in which like elements in different figures have like reference numerals. The figures, which are not necessarily to scale, depict selected embodiments and are not intended to limit the scope of the invention. Skilled artisans will recognize the examples provided herein have many useful alternatives fall within the scope of the invention.

In general, the present invention applies to exercising a primary or secondary battery cell that, for whatever reason, has not recently discharged (e.g., delivered or drained) enough electrical energy sufficient to remove a resistive film that typically forms on at least a portion of an electrode thereof. Such a film unfortunately produces delayed discharge thereby negatively affecting rapid or high-rate discharge performance of the battery. For certain battery applications such delayed discharge can significantly and adversely affect the performance of electrical circuitry powered by the battery. One such application involves rapid charging one or high voltage capacitors operatively coupled to an implantable cardioverter-defibrillator (ICD). Once fully charged such capacitors must rapidly and precisely fully discharge a potentially life-saving therapeutic cardioversion or defibrillation charge through a defibrillation vector defined by a pair of defibrillation electrodes disposed near a heart.

However, while the illustrations and written description utilize the context of medical devices, the present invention should not be construed as so limited. For example, while cardioverter defibrillators, including ICDs, will benefit from the teaching hereof, many various types of implantable and external electronic and mechanical devices can advantageously utilize the present invention. In the context of medical devices, any device for treating patient medical conditions such as pacemakers, defibrillators, neurostimulators, therapeutic substance delivery pumps and the like can benefit from the present invention. For purposes of illustration only, however, the present invention is primarily described in the context of an ICD. In addition, while the present invention is not limited to high-current-rate batteries (high-rate batteries)—and may be utilized for low- or medium-rate batteries—the present invention is described herein in the context of high-rate batteries coupled to one or more high voltage capacitors and associated operative circuitry of an ICD.

With reference to FIG. 1, a simple block diagram illustrating an ICD according to an embodiment of the present invention, ICD 10 includes an ICD status system 12, implantable leads 14, a therapy delivery system 16, a battery 18, and an internal bus 20. ICD status system 12 includes a processor or microcontroller 22 and a memory 24 with a software module 25. Memory 24 stores several variables relating to patient monitoring, capacitor performance, ICD performance, and the like, which are not described in detail, as they are peripheral to the core of the present invention. Memory 24 also stores several variables related to battery performance including one of more of the following: battery background voltage, battery loaded voltage, capacitor charge time, time elapsed since last capacitor charge, time elapsed since last battery exercise or conditioning, energy stored on the capacitor during the last charging event, discharge conditions during the last battery exercise or conditioning, other pertinent measures of battery, capacitor and device performance and software to perform various ICD functions including self-tests, algorithms for patient monitoring, therapy delivery and the like. Memory 24 also includes software module 25, which performs battery-exercising functions according to the present invention, which are discussed in more detail below. It is contemplated that the software could be replaced with hardware or firmware or combinations thereof. As illustrated, processor 22 comprises a microprocessor with built in memory; however, it is contemplated processor 22 could be a microcontroller, an ASIC, or a pic controller within the context of the present invention.

Implantable leads 14 include one or more medical electrical conductive cardiac leads having electrodes operatively coupled thereto (e.g., atrial or ventricular pace/sense electrodes, defibrillation electrodes—not shown) as is known and used in the art. One or more of the leads 14 are deployed into electrical communication with a portion of myocardium and adapted to sense and/or deliver therapeutic pacing stimulus. Leads 14 can be deployed to an atrial or a ventricular epicardial site and/or an atrial or ventricular endocardial site and configured for unipolar or bipolar cardiac pacing and sensing.

For the exemplary ICD therapy delivery system 16 includes one or more capacitors 26 and other circuitry (not shown) for delivering or transmitting electrical energy from the battery 18 in measured doses through leads 14 to the myocardium of a heart or to other living tissue. Additionally, therapy delivery system 16 includes one or more timers, analog-to-digital converters, transformers, and other conventional circuitry (not shown) for conveying or measuring various electrical properties related to performance, use, and maintenance of the therapy system. It is contemplated capacitor(s) 26 could be any type of high voltage capacitor, however, as illustrated capacitor(s) 26 comprise low- to no-reformation capacitors such as wet-tantalum capacitors.

Generally, leads 14 sense atrial or ventricular electrical activity and provide data representative of this activity to monitoring system processor 22. Processor 22 processes this data according to software instructions in memory 24. If appropriate, processor 22 then directs therapy delivery system 16 to deliver one or more measured doses of electrical energy or other therapeutic agents through leads 14 to a patient's heart.

As used herein, battery 18 includes a single primary electrochemical cell or cells. Battery 18 is volumetrically constrained in the sense that the components in the case of battery 18 cannot exceed the available volume of the battery case. A discussion of the various considerations in designing the electrodes and the desired volume of electrolyte needed to accompany them in, for example, a lithium/silver vanadium oxide (Li/SVO) battery appears in U.S. Pat. No. 5,458,997 issued to Crespi et al. Generally, however, the battery 18 must include the electrodes and additional volume for the electrolyte required to provide a functioning battery.

Figure 2:
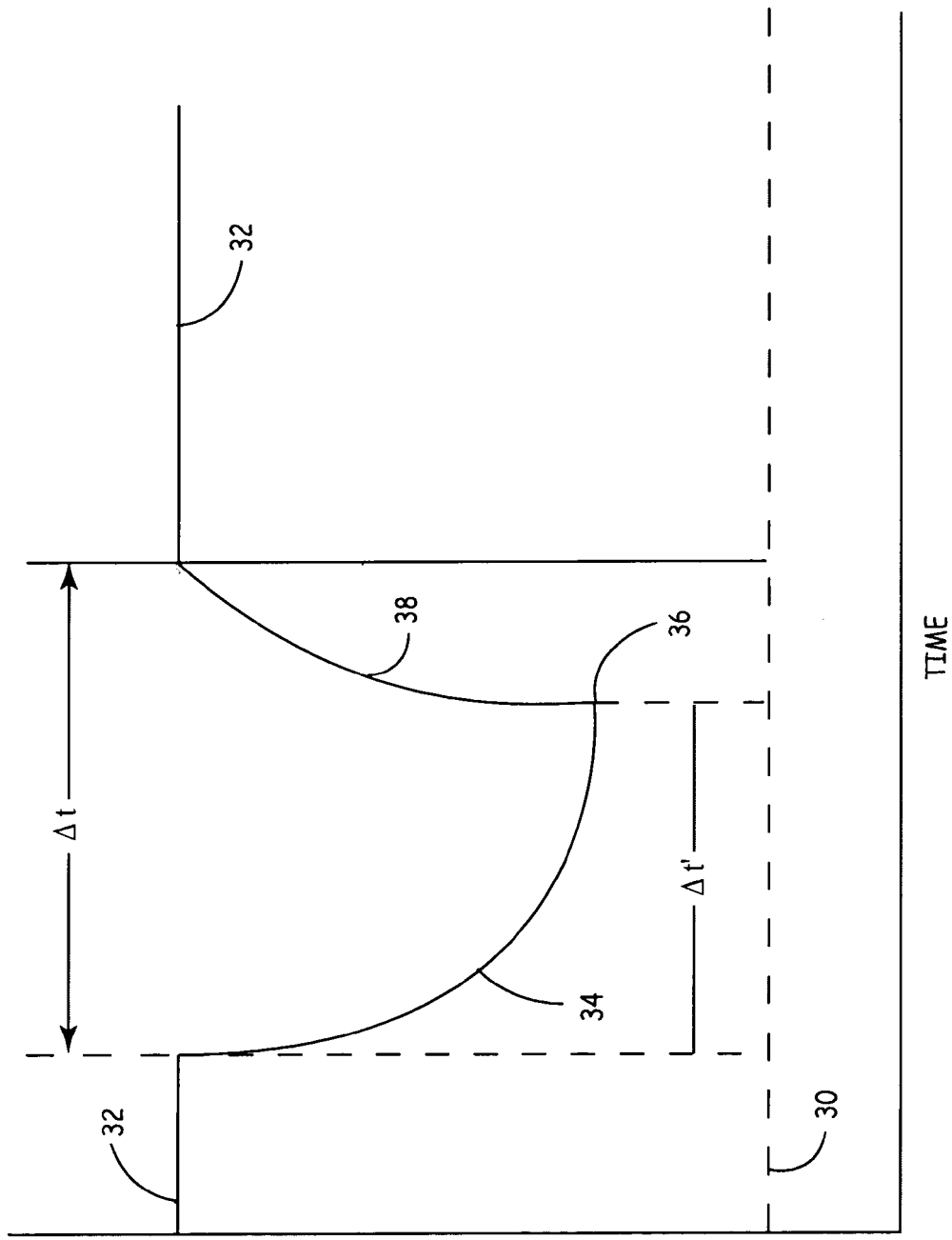
FIG. 2 graphically depicts a battery voltage curve for a battery operatively coupled to an implantable cardioverter defibrillator over a time when a high current drain event occurred, such as the battery charging a capacitor to deliver a high voltage defibrillation therapy and the battery did not have a resistive film disposed over an electrode thereof.

With reference to FIG. 2 which graphically depicts battery voltage curve for a battery 18 operatively coupled to an ICD over a time when a high current drain event occurred, such as the battery 18 charging a capacitor 26 to deliver a high voltage defibrillation therapy and said battery 18 does not have a resistive film disposed over an electrode thereof. The graph depicted in FIG. 2 shows a voltage curve for a battery 18 operatively coupled to an ICD 10 over period of time wherein a therapy requiring a relatively high-rate discharge of the battery 18. Basically, the graph displays battery voltage over time with a dashed line representing a voltage floor 30. The upper limit of the battery voltage is indicated by an upper, substantially flat, line 32 illustrating the average high voltage of battery 18 during operation of ICD 10. If processor 22 detects the patient is in need of an electrical therapy and then initiates therapy delivery, a signal is sent to therapy delivery system 16 to rapidly charge capacitor 26. The charging of capacitor 26 puts a large-drain load on battery 18 as represented by downward curve 34 stemming from the upper line 32. When capacitor 26 is charged to a desired maximum or rated voltage the large-drain load ceases, as represented by point 36, and the battery 18 begins to recover to the upper limit of battery voltage 32, as represented by upward curve 38. Notably, the graph depicted in FIG. 2 represents a battery 18 absent any film buildup or a very small film buildup as discussed above. Since there is a limited film buildup, battery 18 is able to quickly provide the voltage as required to rapidly and fully charge the capacitor 26. The total time required for battery 18 to provide the full charge of capacitor 26 and then recover is represented by $\Delta t$ and the total time required to supply voltage to capacitor 16 to provide a therapy is represented by $\Delta t'$. Generally, it is desired for $\Delta t'$ to equal approximately 10 seconds or less to ensure successful therapy delivery.

Figure 3:
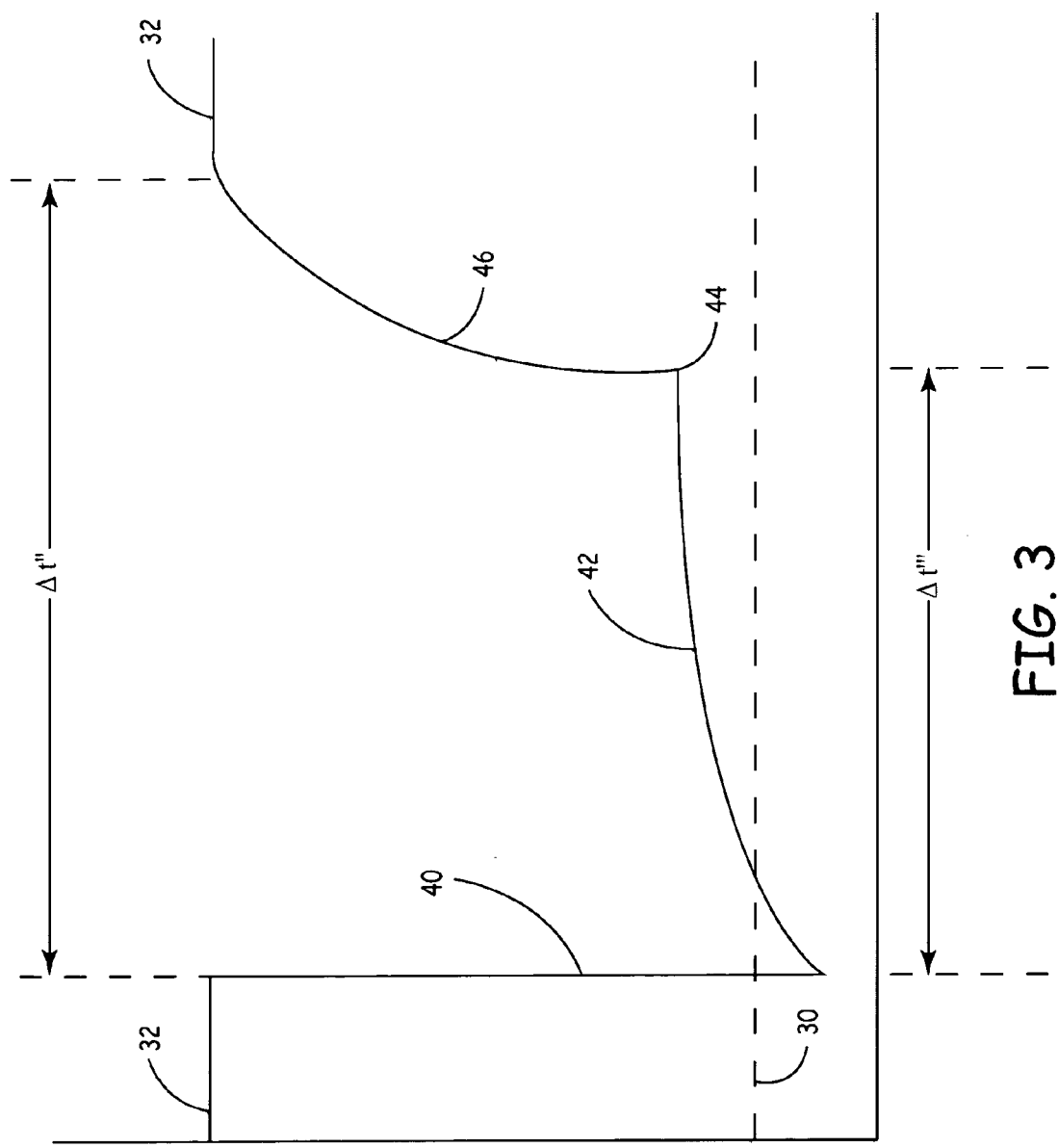
FIG. 3 graphically depicts a battery voltage curve for a battery operatively coupled to an implantable cardioverter defibrillator over a time when a high current drain event occurred such as the battery charging a capacitor to deliver a high voltage defibrillation therapy and a resistive film was disposed over at least a portion of an electrode of the battery.

FIG. 3 graphically depicts a battery voltage curve for a battery 18 operatively coupled to an ICD 10 over a time when a high current drain event occurred such as the battery 18 charging a capacitor 26 to deliver a high voltage defibrillation therapy when a resistive film was disposed over at least a portion of an electrode of the battery 18. That is, the graph depicted in FIG. 3 illustrates how the battery voltage varies over time when film is present on an electrode thereof. Thus, FIG. 3 represents a common situation wherein a film has grown on an electrode of battery 18. Similar to the discussion above, if processor 22 detects the patient is in need of an electrical therapy and then initiates therapy delivery, a signal is sent to therapy delivery system 16 to charge capacitor 26. Straight vertical line 40 represents the situation where capacitor 26 has is receiving energy from battery 18; however, the resistive film acts to delay or block any substantial energy transfer. Therefore, capacitor 26 quickly takes the battery voltage to a low level, even beyond voltage floor 30 as represented in FIG. 3. Fortunately, the rapid drain of energy from the battery 18 operates to substantially remove the film from the electrode. Thus, as the film begins to slough off the voltage of battery 18 gradually begins to increase as represented by upwardly curving line 42. Therefore, capacitor 26 has difficulty getting charged rapidly because the resistive film reduces or impedes, at least initially, the high-current drain from battery 18. In addition, for certain ICDs a therapy delivery preserving circuit can control or restrict energy transfer from battery 18 to capacitor 26 (as represented by curve 42 in FIG. 3 as the voltage rises above voltage floor 30). Once the voltage (i.e., as represented by curve 42 rises above voltage floor 30, the therapy delivery protection of the ICD ends and capacitor 26 can begin fully charging once again. This phenomenon is represented by curve 42 leveling off above voltage floor 30. When capacitor 26 is finished charging, as represented by fiducial point 44, battery 18 begins to recover to its full voltage (as depicted by substantially horizontal line 32) as shown by upwardly curving line 46. The total time required for battery 18 to charge capacitor 26 and then recover is represented by $\Delta t''$ and the total time required to supply sufficient voltage to capacitor 16 to provide a therapy is represented by $\Delta t'''$. As can be seen from FIG. 3, it takes substantially longer to charge capacitor 26 when one or more electrodes of the battery 18 is covered by a resistive film than not (as depicted in FIG. 2). This condition is highly undesirable in the context of ICD operation—as well as certain other medical and non-medical devices—as the longer it takes to prepare to perform a time sensitive operation (e.g., deliver a high voltage therapy), the less likely the operation will be successful. In the context of an ICD, the higher degree of hemodynamic compromise and, oftentimes, the lower the chances of successful defibrillation and/or cardioversion therapy delivery. Further, the total charge and recover time represented by $\Delta t''$ is much longer as well.

Figure 4:
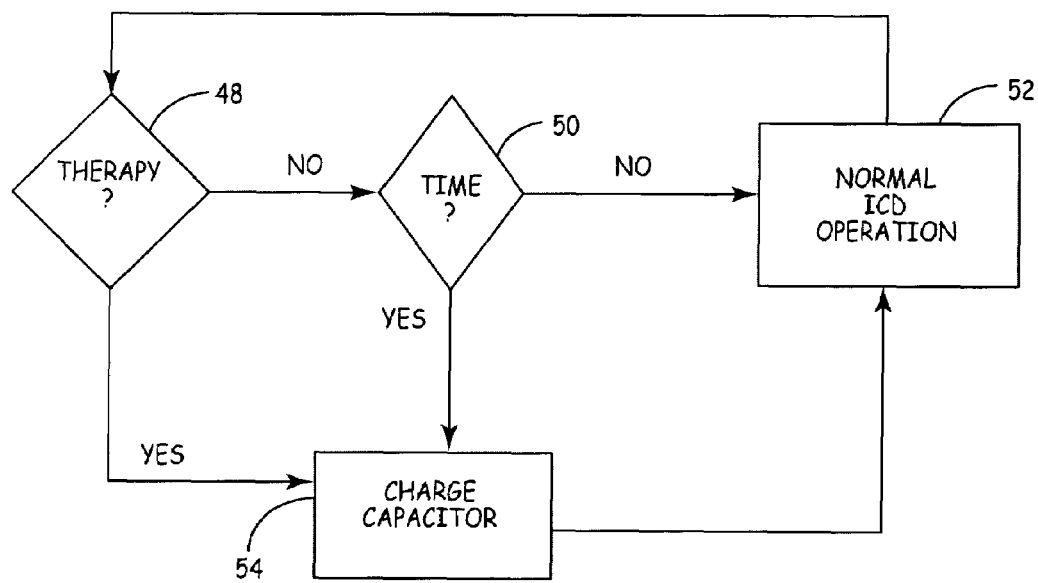
FIG. 4 depicts a process flowchart illustrating an embodiment of the present invention for exercising a battery to relieve the resistive film disposed on an electrode of the battery.

FIG. 4 depicts a process flowchart illustrating an embodiment of the present invention for exercising a battery to relieve the resistive film disposed on an electrode of the battery. That is, FIG. 4 depicts a single embodiment of a battery-exercising method according to the present invention. As stated above it is undesirable to have a film build up in battery 18 as this can case cause delay in performing an operation requiring a rapid drain of a battery (e.g., charging a high voltage capacitor). As described and depicted herein, the inventors have discovered that for certain situations it is highly desirable to "exercise" a battery 18 to prevent, or relieve any, film buildup within a battery 18. The flowchart represented in FIG. 4 shows a simple embodiment of the present invention where the battery exercising is somewhat inflexible. To begin the battery exercising process, based on sensed signals of cardiac depolarizations (or lack thereof) processor 22 determines if a cardiac therapy is scheduled to occur (as shown in FIG. 4 by state 48). If a cardiac therapy is scheduled, processor 22 instructs therapy delivery system 16 to prepare for delivery of said therapy (e.g., fully charge capacitor 26 in order to deliver the therapy). This prevents any battery exercising from interrupting the timing of delivery of a potentially crucial therapy. If a therapy is not scheduled, then processor 22 proceeds to state 50 (which schematically represents a timing utility or procedure). At state 50 processor 22 determines how much time has elapsed since the last therapy was administered to a patient or how long it has been since the most recent battery exercising session. If less than a predetermined period of time (e.g., three months) has elapsed since the most recent therapy delivery or battery exercising, processor 22 resumes normal ICD 10 operation as represented in state 52. Processor 22 will then wait a second predetermined time (e.g., one month) before returning to state 48 to once again determine whether a therapy is needed before determining when the last therapy or exercising occurred.

Generally, for certain ICD applications a three-month timeframe is short enough so only a small amount of film buildup will occur. Further, given a small amount of film buildup the inventors posit that a relatively smaller amount of power is required to exercise battery 18 to remove the film buildup than if a heavy film had accumulated. However, the inventors fully contemplate that a longer or shorter time frame for exercising the battery could be utilized (e.g., one, six, nine twelve months) without departing from the teaching of the present invention. At these longer time intervals a chance exists that a patient might require a high voltage therapy delivery before the exercising takes place and therefore, there is a chance a larger film buildup will be present in comparison to the three-month time interval. Further, at longer time intervals the exercising of battery 18 will require more power to relieve the electrode(s) of the film. With reduced time frames a lower chance exists that a large film buildup will occur; however, the more frequent exercising of battery 18 might deplete battery 18 quicker than a longer time frame between therapies and exercising. Optimizing the time intervals between therapies and/or battery exercising based on the behavior of a particular battery/device system tends to maximize the longevity of a device while maintaining short therapy charge times.

If the time interval since a prior therapy or exercising is greater than three months, then processor 22 instructs therapy delivery system 16 to partially charge capacitor 26 with a predetermined relatively low amount of energy relative to the maximum or rated energy of a typical high voltage capacitor 26. Thus, the capacitor 26 can be charged to about 2.5 J, as shown in state 54. The inventors have found that 2.5 J of energy works well at a three month time frame. However, it is fully contemplated any relatively reduced amount of energy could be utilized without departing from the spirit of the invention. Importantly, it is not required for battery 18 to charge a capacitor 26 to perform the battery exercising. In fact, a number of different ways exist to perform the battery exercising of the present invention in an energy efficient manner without utilizing any capacitor.

As noted above, the capacitor 26 need only be partially charged (relative to a maximum or rated voltage of the capacitor) since only a small amount energy drain is required to exercise battery 18 to thereby recover its nominal film-free performance. Therefore, during battery exercising battery 18 could charge capacitor 26 to a very low energy as stated above, discharge battery 18 through a non-therapeutic resistive load, or charge a so-called ultra- or super-capacitor and slowly discharge such capacitor to power a device (e.g., an ICD 10). The benefits of the present invention are two-fold. First, battery 18 is maintained at an optimal voltage level and second the amount of power used to exercise battery 18 is minimal when compared to the power used to reform a deformed or degraded dielectric oxide layer disposed in and about the anode electrode of high voltage capacitors. If processor 22 fully charges capacitor 26 to exercise the battery 18, too much energy is used to exercise battery 18 than necessary to improve the performance of the battery 18. Therefore, the present invention allows for improved battery performance thereby providing lower capacitor charge times, lower internal battery resistance, and lower overall energy consumption—all without paying the high price (or system energy cost) of fully charging capacitor 26. After completing battery exercising operations, ICD 10 returns to state 52 from state 54 to resume normal ICD operation.

The battery exercising method represented in FIG. 4 is somewhat inflexible in that the time frame and power for exercising is set. More flexible battery exercising methods are discussed hereinbelow, which are intended to introduce the uninitiated to several related, alternate embodiments of the present invention. Upon reflecting upon these embodiments those of skill in the art of battery-powered devices will surely recognize other embodiments and/or contemplate slight changes to the alternate embodiments. All such embodiments are expressly deemed covered by this disclosure of the present invention.

Figure 5:
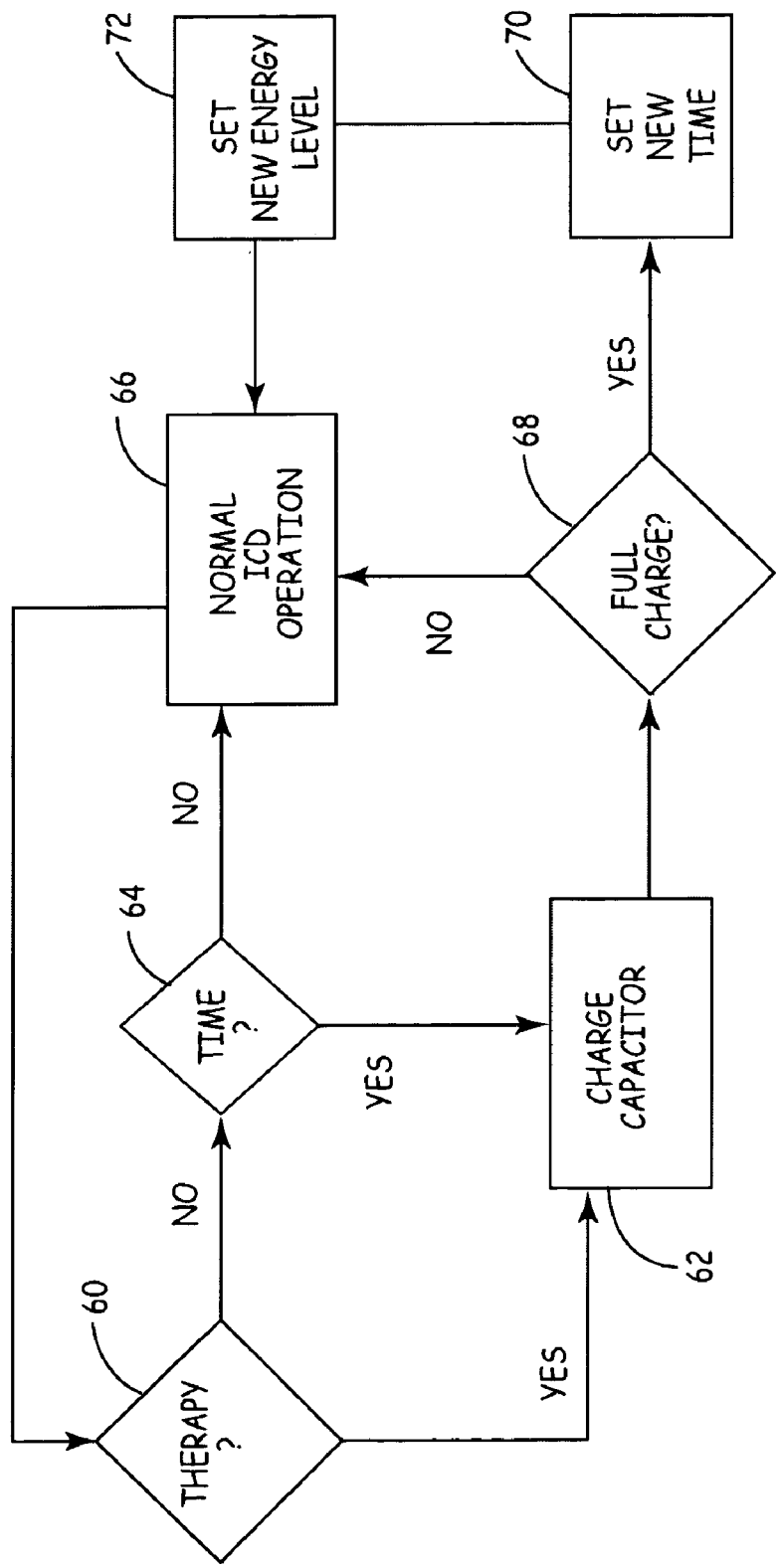
FIG. 5 depicts a process flowchart illustrating another embodiment of the present invention for exercising a battery to relieve the resistive film disposed on an electrode of the battery.

FIG. 5 depicts a process flowchart illustrating another embodiment of the present invention for exercising a battery to relieve the resistive film disposed on an electrode of the battery. The battery exercising process depicted in FIG. 5 optimizes the energy used to exercise and the timeframe between exercising/therapies to extend the operating life of ICD 10. Similar to the discussion above, the battery exercising process first starts by determining if a cardiac therapy is scheduled (including if an arrthymia detection sequence has been initiated) as shown at state 60. If a therapy is scheduled (or detection sequence underway), processor 22 instructs therapy delivery system 16 to fully charge capacitor 26 in order to deliver a therapy as shown in state 62. If a therapy is not scheduled, then processor 22 proceeds to state 64. At state 64 processor 22 determines how long it has been since the most recent therapy was administered to a patient and how much time has elapsed since the last battery exercising session. If the last therapy or exercising was less than one month ago, processor 22 resumes normal ICD 10 operation as represented in state 66. Processor 22 will then wait a predetermined interval of time (e.g., three weeks) and then return to state 60 to again determine whether a therapy is needed before determining when the last therapy or exercising occurred.

If the most recent therapy delivery or battery exercising occurred more than a predetermined amount of time ago (e.g., a month or x-weeks), then processor 22 instructs therapy delivery system 16 to partially charge capacitor 26 with a predetermined amount of energy as represented in state 62. In the embodiment of FIG. 5, processor 22 executes an optimization software module 25 (see FIG. 1) having algorithms, which minimize the amount of energy removed from the battery 18 based on voltage delay. The software module 25 can be based on several battery and capacitor charge variables without departing from the teaching of the present invention. For example, software module 25 could be based on capacitor charge time, wherein if the charge time exceeds a certain threshold, then the battery exercising voltage and/or the time frame between exercising is modified. At state 68 processor 22 determines whether capacitor 26 was fully charged or if it was charged with a smaller energy such at 2.5 J as discussed in the embodiment of FIG. 4. If processor 22 determines the capacitor charge was less than a full charge, then software module 25 returns to state 66 and sets a longer exercising time, for example three months. The process then begins again and if after three months no therapy or battery exercising has occurred, then processor 22 once again instructs battery 18 to apply a small charge to capacitor 26. Software module 25 then determines whether a full charge was administered and if not, then software module 25 returns to normal ICD operation (at state 66).

Generally, software module 25 optimizes the amount of energy removed from battery 18 through modification of the exercising voltages and the time frames between exercising to determine through experimentation the optimal exercising voltage and the timing between battery exercising events. A conditioning discharge event would be performed thus exercising the battery 18 at one month, three month, six month, and twelve-month increments (or other schedule) at a particular energy level for example a 2.5 J pulse, a 15 J pulse, or a 32 J pulse (or the like). Then periodically, a therapy is administered or the capacitor is fully charged to measure the voltage delay. When the full charge is discovered at state 68 software module 25 can then adjust the interval between exercising at state 70 and/or the level of energy for the exercising at state 72, based upon the measured voltage delay. For example, if no voltage delay is detected, then software module 25 can maintain the exercising voltage and extend the time frame between exercising battery 18 and/or lower the exercising voltage. If a voltage delay is detected, then the time frame between exercising battery 18 could be lowered and/or the exercising voltage could be increased. Software module 25 will then track what exercising time frames are used and what exercising voltages are being used to optimize the exercising process. Software module 25 then stores the different amounts of energy required depending upon how long it's been since the last pulsing or the capacitor thus creating a map (e.g., data set or relational database) for an optimum regime based on how a particular ICD 10 operates. Software module 25 insures the exercising treatment uses as little energy as possible to optimize the total energy available from battery 18 thereby potentially extending the operating life of the ICD 10.

In addition, ICD 10 can be interrogated to obtain the data set indicating the optimal battery exercising timeframes and energy-release levels to be. Then, a next set of ICDs can be programmed prior to implementation with an existing data set storing exercising timeframe(s) and energy level(s) with reference to the optimized timeframe(s) and energy level(s) and thereby require less testing to employ near-optimal exercising timeframe(s) and energy level(s) for a particular battery 18. A physician would be able to program in the different energy levels and time frames. Of course, while the present invention is described and depicted herein as a part of medical device system having a single battery, no such limitation should be inferred therefrom. Indeed, the present invention hereby expressly claims such multi-battery device systems, including such systems having more than one primary and/or secondary batter operative coupled thereto.

Figure 6:
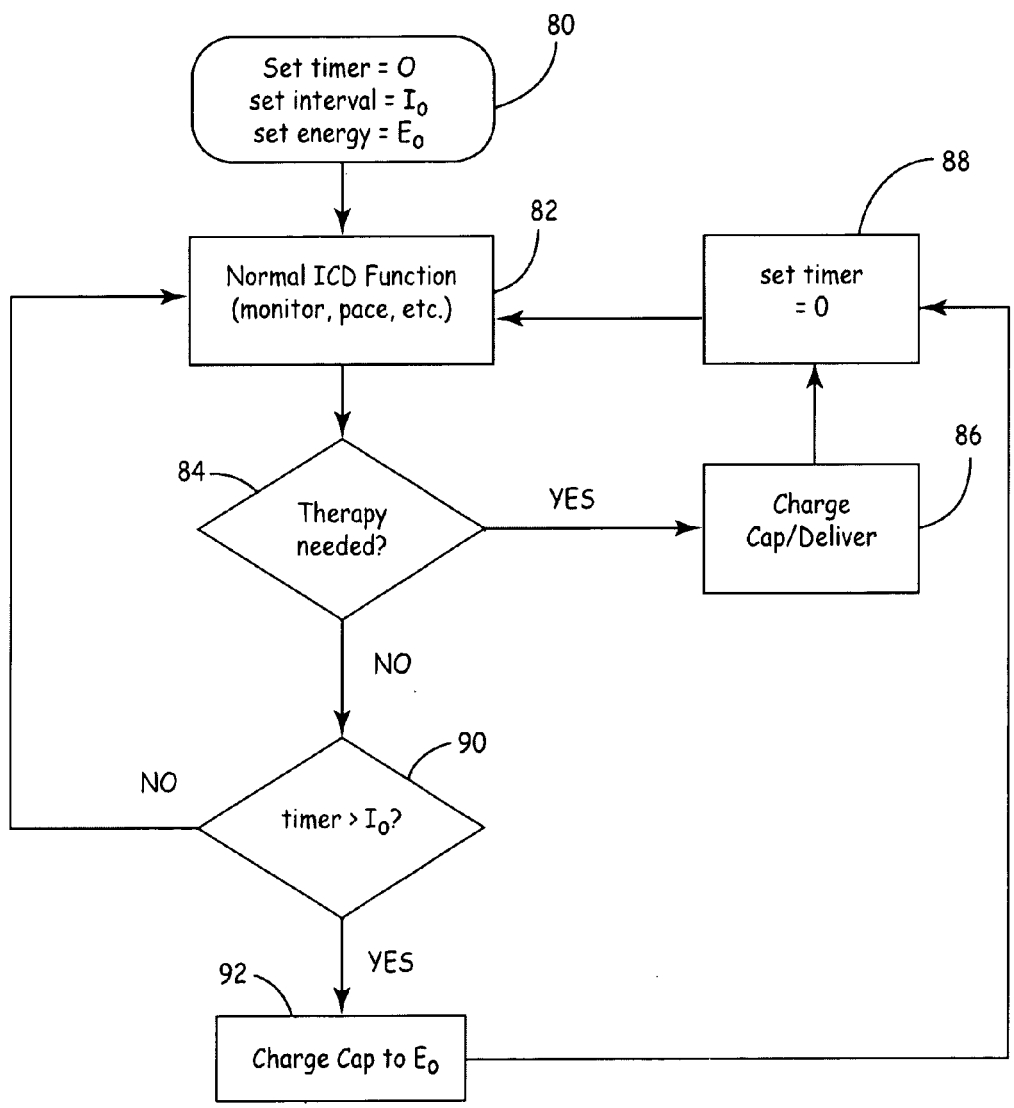
FIG. 6 depicts a process flowchart illustrating another embodiment of the present invention for exercising a battery to relieve the resistive film disposed on an electrode of the battery.

FIG. 6 depicts a process flowchart illustrating another embodiment of the present invention for exercising a battery to relieve the resistive film disposed on an electrode of the battery. As illustrated in FIG. 6, the process begins at initialization step 80 by setting a timer to a null (or a nominal value), 0, setting an interval timer to null (or a nominal value), $I_o$, and setting an energy indicator to null (or a nominal value), $E_o$. Then, at step 82 normal operation of an ICD 10 begins as is known and employed in the art. As before, at step 84 a determination is made whether or not a therapy is scheduled (or an arrthymia detection sequence is in process) and if affirmative, then a capacitor charging process (and, as applicable, therapy delivery) occurs at step 86 and the timer is reset to a null or nominal value at step 88 before resuming normal ICD operation at step 82. However, if no therapy is scheduled (or being confirmed), then the process proceeds to step 90 wherein the value of the interval timer is evaluated. If the interval timer is not greater than the null (or nominal value) then the process proceeds to step 82, normal ICD operation. If the interval timer is greater than the null value then the capacitor 26 is charged to a nominal energy value, $E_o$. As described herein, the process of nominally charging the capacitor relieves the electrode of the layer of resistive film so that the battery 18 will not suffer the discharge time delay in the event that a high current drain event requires rapid discharge of the battery 18.

Figure 7:
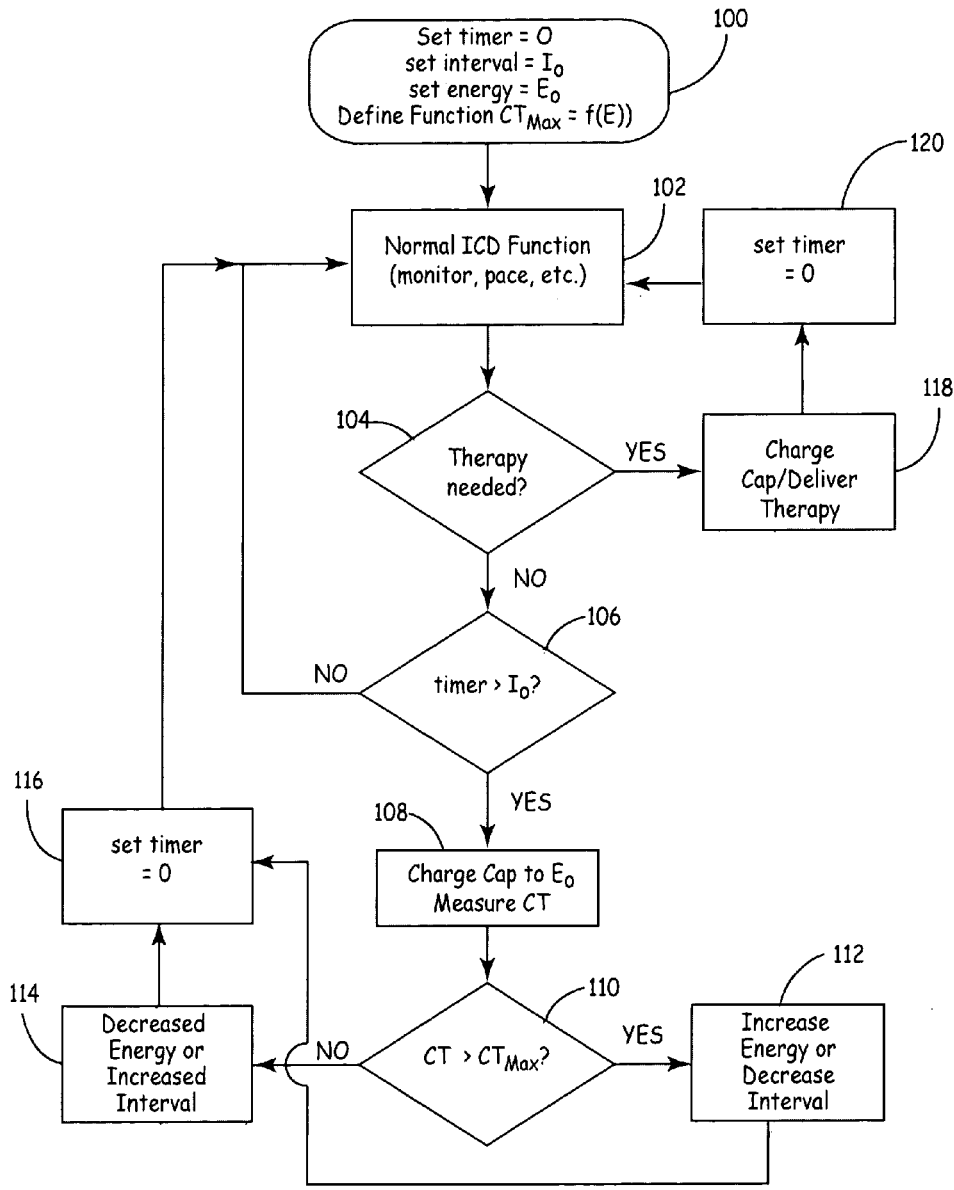
FIG. 7 depicts a process flowchart illustrating yet another embodiment of the present invention for exercising a battery to relieve the resistive film disposed on an electrode of the battery.

FIG. 7 depicts a process flowchart illustrating yet another embodiment of the present invention for exercising a battery to relieve the resistive film disposed on an electrode of the battery. As illustrated in FIG. 7, the process begins at initialization step 100 by setting a timer to a null (or a nominal value), 0, setting an interval timer to null (or a nominal value), $I_o$, setting an energy indicator to null (or a nominal value), $E_o$, and defining a capacitor charging time as function of energy (e.g., $CT_{max}$=f(E)). Then, at step 102 normal operation of an ICD 10 begins as is known and employed in the art. As before, at step 104 a determination is made whether or not a therapy is scheduled (or an arrthymia detection sequence is in process) and if affirmative, then a capacitor charging process (and, as applicable, therapy delivery) occurs at step 118 and the timer is reset to a null or nominal value at step 120 before resuming normal ICD operation at step 102. However, if no therapy is scheduled (or being confirmed), then the process proceeds to step 106 wherein the value of the interval timer is evaluated. If the interval timer is not greater than the null (or nominal value) then the process proceeds to step 102, normal ICD operation. If the interval timer is greater than the null value then the capacitor 26 is charged to a nominal energy at step 108 to a value, $E_o$, and the time required to achieve the nominal energy value is measured. Then, at step 110 the measured charge time (CT) is compared to the value of $CT_{max}$ and if CT exceeds $CT_{max}$, then at step 112 either the energy is increased from the nominal setting or the interval timer is decreased to a new value (or both). However, if at step 110 the value of CT does not exceed $CT_{max}$, then the process proceeds to step 114 wherein the energy is decreased from the nominal setting or the interval timer is increased to a new value (or both). Following performance of either step 112 or 114, the process proceeds to step 116 and the timer is set of a null (or nominal value) before returning to step 102, normal ICD operation.

As described herein, the process of nominally charging the capacitor relieves the electrode of the layer of resistive film so that the battery 18 will not suffer the discharge time delay in the event that a high current drain event requires rapid discharge of the battery 18.

Figure 8:
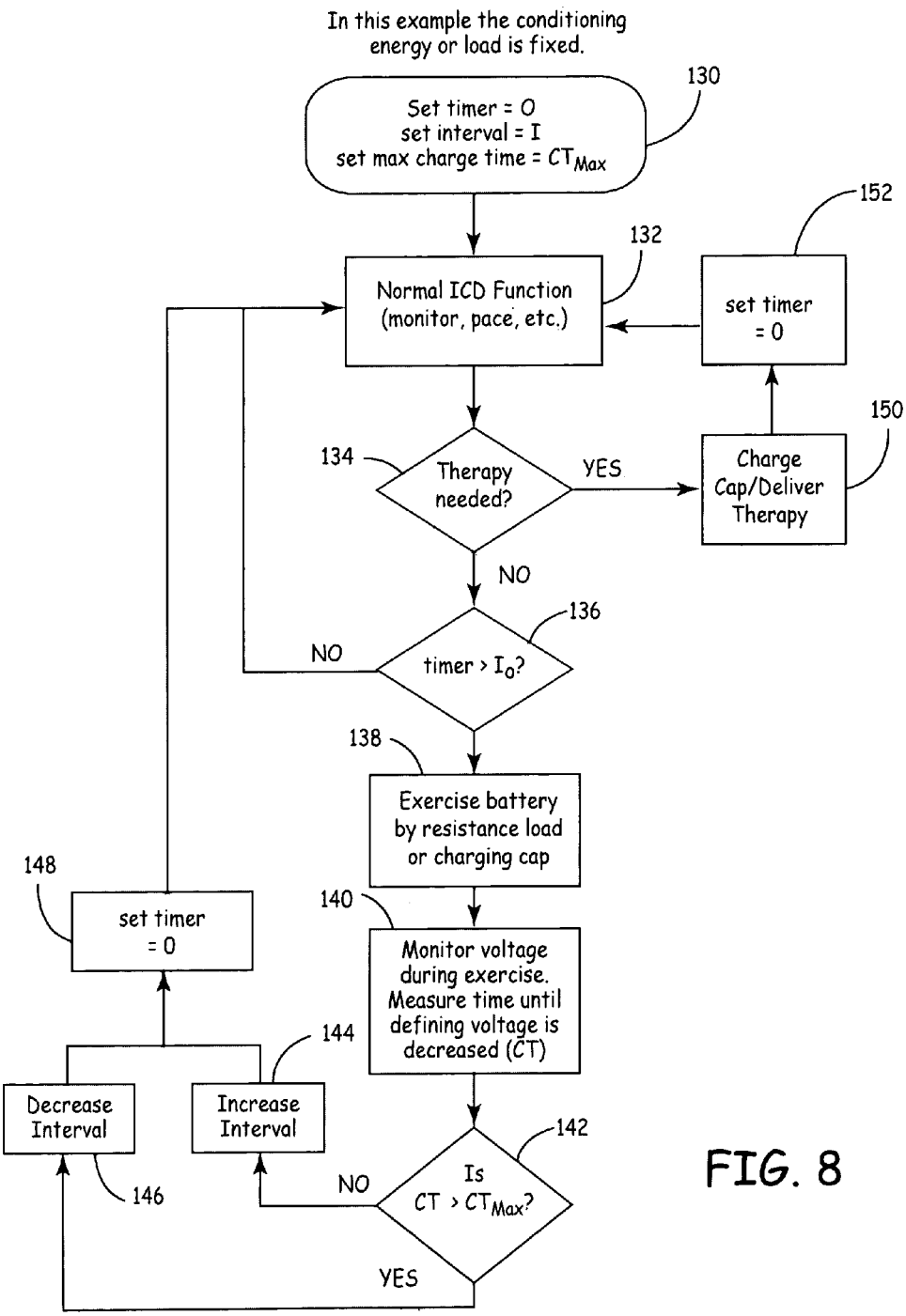
FIG. 8 depicts a process flowchart illustrating a further embodiment of the present invention for exercising a battery to relieve the resistive film disposed on an electrode of the battery.

FIG. 8 depicts a process flowchart illustrating yet another embodiment of the present invention for exercising a battery to relieve the resistive film disposed on an electrode of the battery. As illustrated in FIG. 8, the process begins at initialization step 130 by setting a timer to a null (or a nominal value), 0, setting an interval timer to null (or a nominal value), $I_o$, and setting a maximum charging time, $CT_{max}$. The maximum charging time can be set with reference to a maximum or rated voltage of one or more capacitors operatively coupled to energize an ICD. Then, at step 132 normal operation of an ICD 10 begins as is known and employed in the art. As before, at step 134 a determination is made whether or not a therapy is scheduled (or an arrthymia detection sequence is in process) and if affirmative, then a capacitor charging process (and, as applicable, therapy delivery) occurs at step 150 and the timer is reset to a null or nominal value at step 152 before resuming normal ICD operation at step 132. However, if no therapy is scheduled (or being confirmed), then the process proceeds to step 136 wherein the value of the interval timer is evaluated. If the interval timer is not greater than the null (or nominal value) then the process proceeds to step 132, normal ICD operation. If the interval timer is greater than the null value then the battery 18 is exercised without utilizing a capacitor 26. For example, at step 138 a battery 18 can be exercised by a rapid albeit short, high-rate discharge distributed through a non-therapeutic load, such an electrical resistor or by charging a ultra- or super capacitor (not shown) either partially or fully. In the latter case, the charge stored in the capacitor can be utilized for carrying out various operations of the ICD 10. One such use can involve providing sufficient power for short-term or extended telemetry to a remote, external device. Alternatively, the power can be used to provide pacing and/or sensing operations for low power pacing therapy, or the like. In any event, while completing step 138 the process proceeds simultaneously to step 140 wherein the voltage of the battery 18 is monitored while the battery is exercised to measure the amount of time elapsed until a declining voltage is observed—during charging of the capacitor 26 (see FIG. 9 for additional details). Then, at step 142 the charging time, expressed as CT, and comprising a time interval until declining voltage is observed, is compared to the maximum charge time ($CT_{max}$). If the charge time, CT, is greater than the maximum charge time $CT_{max}$ then the timing interval is increased at step 146. And, if CT is less than $CT_{max}$ then the interval is increased at step 144. In either event, after performing step 144 or 146 the time is reset of a null (or a nominal value) at step 148 before resuming normal ICD operation at step 132.

While not depicted or described with reference to the foregoing illustrated processes, in the event that a comparison renders an equivalent result, an indeterminate result is obtained. Such a result may be handled in a number of ways; however, those of skill in the art will recognize that such a result albeit unlikely can be accommodated by returning to the prior step after a preset time and re-executing the step that initially caused in the indeterminate result.

Figure 9:
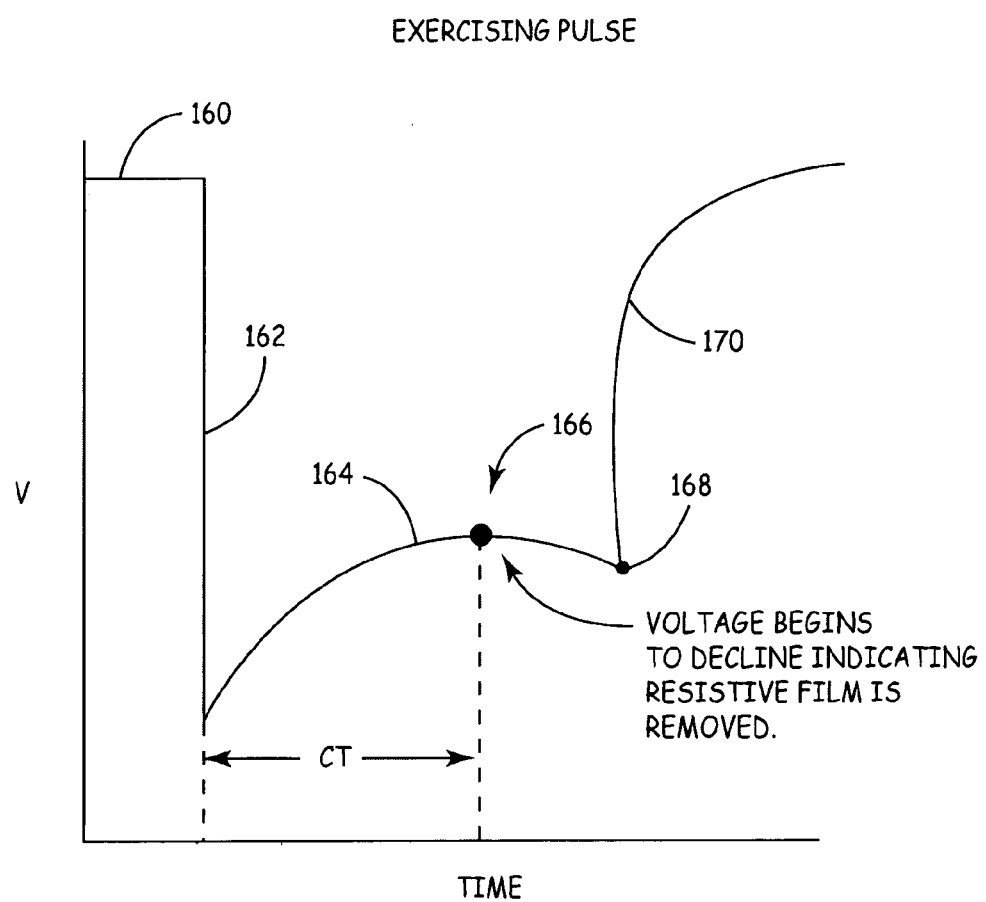
FIG. 9 graphically depicts a voltage curve for a battery exercising pulse according to the present invention illustrating a fiducial point indicative of the effective removal of a resistive film from an electrode of the battery.

FIG. 9 graphically depicts a voltage curve 160, 162, 164, 170 for a battery exercising pulse according to the present invention illustrating a fiducial point 168 indicative of the effective removal of a resistive film from an electrode of the battery 18, as briefly described with reference to FIG. 8, above. That is, FIG. 9 is a slightly more refined representation of the effects of and morphology of an effective battery exercising pulse according to the present invention. In FIG. 9, the time interval ("CT") denotes the time during which the capacitor 26 is charged sufficiently to remove the resistive film. Thus, as the resistive film is being removed the portion 164 of the voltage curve of the battery 18 rises asymptotically to a fiducial point 166. As will be appreciated by those of skill in the art this phenomenon indicates that the current drain from the battery 18 is not being effectively transferred to the capacitor 26. In this regard, compare FIG. 2 to FIG. 9. That is, rather than falling in an exponential-like decay over segment 164 of FIG. 9 (like segment 34 of FIG. 2), the battery voltage actually rises. At fiducial point 166, the voltage of the battery finally begins to decrease thereby indicating that the capacitor 26 is more effectively absorbing charge from the battery 18. Then, when the capacitor 26 achieves its maximum or rated voltage (at transition point 168) the voltage of the battery 18 rises rapidly (as illustrated by segment 170). Note that the segment 170 is roughly equivalent to the segment 38 of FIG. 2, which also indicates a fully charged capacitor 26 (albeit a capacitor that never suffered charging performance difficulties due to resistive film disposed on electrode of the battery 18).

It will be appreciated the present invention can take many forms and embodiments. The true essence and spirit of this invention are defined in the appended claims, and it is not intended the embodiment of the invention presented herein should limit the scope thereof.

The invention claimed is:

1. An implantable medical device for implantation into a patient, comprising:
    a battery having an electrode that develops a resistive film;
    a low deformation-rate capacitor capable of storing a charge from the battery, the capacitor requiring few or no periodic discharges of the battery for reformation;
    means for periodically discharging energy from the battery into the low deformation-rate capacitor to reduce film buildup on the electrode; and
    means for optimizing the battery discharge.

2. An implantable medical device according to claim 1, further comprising a lead for sensing electrical signals of a patient via at least one electrode operatively coupled to the lead.

3. An implantable medical device according to claim 2, further comprising a status system for monitoring heart activity of the patient through the lead.

4. An implantable medical device according to claim 3, further comprising a therapy delivery system for delivering electrical energy through the lead to a heart of the patient.

5. An implantable medical device according to claim 1, further comprising a means for determining time elapsed since a therapy was delivered to a patient or since the battery was at least partially discharged.

6. An implantable medical device according to claim 1, wherein the battery discharge is greater than about 2.5 Joules.

7. An implantable medical device according to claim 1, further comprising a means for optimizing the time between discharging the battery.

8. An implantable medical device according to claim 7, wherein the means for optimizing the battery discharge is dependant upon voltage delay.

9. An implantable cardioverter defibrillator according to claim 1, further comprising a means for optimizing the time between discharging the battery.

10. An implantable cardioverter defibrillator according to claim 9, wherein the means for optimizing the battery discharge is dependant upon voltage delay.

11. An implantable cardioverter defibrillator comprising:
    a lead for applying electrical energy to the patient;
    a battery having an electrode for powering the implantable cardioverter defibrillator, the battery having an electrode that develops a film on it over time due to a lack of battery discharge;
    an ICD status system for monitoring heart activity of the patient through the lead;
    a therapy delivery system for delivering electrical energy through the lead to a heart of the patient;
    a capacitor capable of storing a charge from the battery, the capacitor requiring no periodic discharges of the battery for reformation;
    means for periodically discharging the battery to reduce film buildup on the electrode; and
    means for otimizing the battery discharge.

12. An implantable cardioverter defibrillator according to claim 11, further comprising a means for determining elapsed time since a therapy was delivered to a patient or since the battery was discharged to reduce film buildup.

13. An implantable cardioverter defibrillator according to claim 11, wherein the battery discharge is greater than about 2.5 Joules.

14. A method of exercising a battery of an implantable medical device, comprising:
    determining whether a film is disposed on a portion of an electrode of a battery;
    discharging the battery a sufficient amount to reduce the film disposed on a portion of the electrode of the battery; and
    optimizing energy used during exercising the battery.

15. A method according to claim 14, further comprising: optimizing a time period, wherein said time period is defined as the amount of time elapsed between consecutive exercising of the battery.

16. A method according to claim 14, wherein the energy used during exercising the battery is optimized based upon voltage delay during charging of a capacitor.

17. A method according to claim 14, wherein the energy used during exercising the battery is optimized based upon discharging of the battery.

18. A method according to claim 14, wherein the battery supplies energy to a capacitor or an electrical resistor to exercise the battery.

19. A method according to claim 18, wherein the capacitor charged by the battery subsequently powers the device.

20. A method according to claim 14, wherein the battery is discharged through a resistive load to exercise the battery.

21. A method of exercising a battery of an implantable cardiac defibrillator, comprising:
    determining a period of time elapsed since a cardiac therapy was administered to a patient or since a battery exercising session was performed;
    resuming normal implantable cardiac defibrillator operation if the last therapy or exercising session was less than a predetermined amount of time; and
    charging a capacitor with a predetermined amount of energy if the last therapy or exercising session was performed a greater time than the predetermined time;
    wherein the energy used during exercising the battery is optimized by minimizing the amount of energy removed from the battery.

22. A method according to claim 21, further comprising the step of determining whether the cardiac therapy needs to be administered.

23. A method according to claim 22, further comprising: instructing a therapy delivery system to charge the capacitor to deliver the cardiac therapy on a scheduled basis.

24. A method according to claim 21, wherein the energy used during exercising the battery is optimized by minimizing the amount of energy removed from the battery based on a voltage delay.

25. A method according to claim 24, wherein a processor executes a software module to optimize energy removal from the battery.

26. A method according to claim 21, wherein the energy used during exercising the battery is optimized by minimizing the amount of energy removed from the battery based on a capacitor charge time, wherein said capacitor charge time comprises a period of time during which the capacitor is charged to a maximum or rated voltage of said capacitor.

27. A method according to claim 26, further comprising the step of determining whether the capacitor was charged to the maximum or rate voltage of said capacitor.

28. A computer readable medium for storing instructions for performing a method of exercising a battery of an implantable cardiac defibrillator, comprising:
    instructions for determining a period of time elapsed since a cardiac therapy was administered to a patient or since a battery exercising session was performed;

instructions for resuming normal implantable cardiac defibrillator operation if the last therapy or exercising session was less than a predetermined amount of time;

instructions for charging a capacitor with a predetermined amount of energy if the last therapy or exercising session was performed a greater time than the predetermined time; and instructions for optimizing the energy used during exercising the battery by minimizing the amount of energy removed from the battery.

29. A medium according to claim 28, further comprising instructions for determining whether the cardiac therapy needs to be administered.

30. A medium according to claim 29, further comprising instructions for instructing a therapy delivery system to charge the capacitor to deliver the cardiac therapy on a scheduled basis.

31. A medium according to claim 28, wherein the instructions for optimizing the energy used during exercising the battery comprise instructions for minimizing the amount of energy removed from the battery based on a voltage delay.

32. A medium according to claim 31, wherein a remote processor executes the instructions for optimizing energy removal from the battery.

33. A medium according to claim 28, wherein the instructions for optimizing the energy used during exercising the battery comprise instructions for minimizing the amount of energy removed from the battery based on a capacitor charge time, wherein said capacitor charge time comprises a period of time during which the capacitor is charged to a maximum or rated voltage of said capacitor.

34. A medium according to claim 33, further comprising instructions for determining whether the capacitor was charged to the maximum or rated voltage of said capacitor.

* * * * *